(12) United States Patent
Meyer

(10) Patent No.: US 9,669,436 B2
(45) Date of Patent: Jun. 6, 2017

(54) APPARATUS AND METHOD FOR CLEANING MICROSURGICAL INSTRUMENTS

(71) Applicant: ASICO, LLC., Westmont, IL (US)

(72) Inventor: Rolf Meyer, Biel-Bienne (CH)

(73) Assignee: Asico, LLC, Westmont, IL (US)

( * ) Notice: Subject to any disclaimer, the term of this patent is extended or adjusted under 35 U.S.C. 154(b) by 353 days.

(21) Appl. No.: 14/279,575

(22) Filed: May 16, 2014

(65) Prior Publication Data

US 2014/0246057 A1 Sep. 4, 2014

Related U.S. Application Data

(60) Continuation of application No. 13/739,003, filed on Jan. 11, 2013, now Pat. No. 8,784,569, which is a division of application No. 11/534,573, filed on Sep. 22, 2006, now Pat. No. 8,741,069.

(60) Provisional application No. 60/725,518, filed on Oct. 11, 2005, provisional application No. 60/783,681, filed on Mar. 18, 2006, provisional application No. 60/722,532, filed on Oct. 1, 2005.

(51) Int. Cl.
*B08B 9/032* (2006.01)
*A61B 19/02* (2006.01)
*A61B 1/12* (2006.01)
*A61B 90/70* (2016.01)
*A61F 9/007* (2006.01)

(52) U.S. Cl.
CPC ............ *B08B 9/0321* (2013.01); *A61B 1/126* (2013.01); *A61B 90/70* (2016.02); *B08B 9/032* (2013.01); *A61F 9/007* (2013.01); *Y10T 137/0419* (2015.04)

(58) Field of Classification Search
CPC . A61B 1/121; A61B 190/70; A61B 2090/701; B08B 9/032; B08B 9/0321
USPC ............ 134/22.12, 24, 169 C, 166, 170, 200
See application file for complete search history.

(56) References Cited

U.S. PATENT DOCUMENTS 5,476,454 A * 12/1995 Campbell ................. A61L 2/00
                                                           134/166 C
5,755,894 A *  5/1998 Bowman ................. A61B 1/121
                                                           134/166 C

* cited by examiner

*Primary Examiner* — Saeed T Chaudhry
(74) *Attorney, Agent, or Firm* — Wood, Phillips, Katz, Clark & Mortimer

(57) ABSTRACT

A cleaning apparatus for microsurgical instruments has a flush chamber closed off at one end by a first plug adapted to liquid-tightly grip one end of the instrument, allowing a portion of the instrument to extend past the first plug and out of the flush chamber. The other end of the flush chamber is closed off by a second plug having an inlet port. Liquid injected through the inlet port on the second plug passes through an internal passageway formed in the instrument and exits the instrument through the portion that extends past the first plug. In another embodiment the instrument has an internal passageway and an end cap through which flushing ports are formed which communicate with the passageway. A first plug having an inlet port is liquid-tightly attached to the end cap and liquid injected into the first plug passes through the plug, through the flushing ports and through the passageway to clean detritus from the instrument.

12 Claims, 12 Drawing Sheets

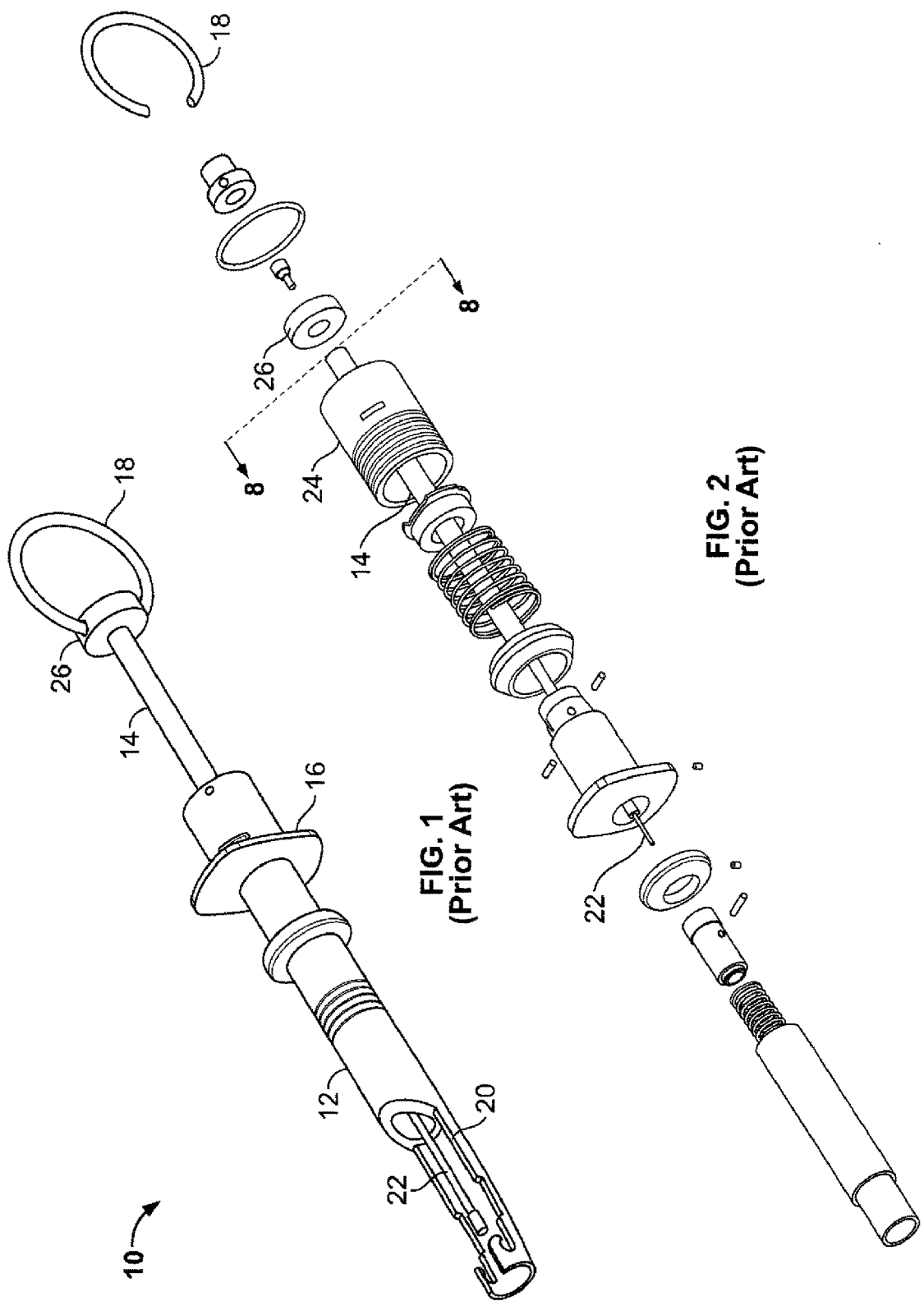

APPARATUS AND METHOD FOR CLEANING MICROSURGICAL INSTRUMENTS

This application is a continuation of U.S. patent application Ser. No. 13/739,003, filed Jan. 11, 2013, which is a division of U.S. patent application Ser. No. 11/534,573, filed Sep. 22, 2006, and claims priority from U.S. Provisional Patent Application Ser. No. 60/783,681, filed Mar. 18, 2006, U.S. Provisional Patent Application Ser. No. 60/725,518, filed Oct. 11, 2005, and U.S. Provisional Patent Application Ser. No. 60/722,532, filed Oct. 1, 2005, all of which are entitled, "Apparatus and Method for Cleaning Microsurgical Instruments", and all of which are incorporated herein in their entirety by reference.

FIELD OF THE INVENTION

The present invention relates generally to microsurgical instruments and, more particularly, to methods and apparatus for cleaning such instruments prior to sterilization.

BACKGROUND OF THE INVENTION

Sterilization of surgical instruments and apparatus is an absolutely essential step in the performance of successful surgeries. Where surgical instruments such as knives, scalpels and the like are used, sterilization is facilitated by the fact that such instruments have no moving parts, leaving all operative surfaces exposed to sterilizing solutions and sterilizing steam or other heated gases.

Ophthlamological surgical techniques involve the use of extremely small instruments commonly referred to as "microsurgical instruments." Many of these instruments not only have moving parts, but have parts that are placed within tubes or other channels. One example of such an instrument is known as a cartridge injector, an instrument used to accept a cartridge within which an intraocular lens (IOL) is folded and placed. A plunger in the injector is then moved through a channel to extend a plunger tip which contacts the lens and forces it through an opening at the end of a cartridge and into an incision formed in the eye.

Another commonly used microsurgical instrument is a microforceps. In this instrument, a pair of opposed surgical steel "strips" extend from a hollow tube. The tube, in turn, is attached to a carriage within the instrument and a handle linkage and mechanism which, when operated moves the carriage and, thereby, the tube forward to contact the two surgical steel strips to force them together. When the handle mechanism is relaxed, the tube is allowed to move rearwardly and the strips then separate.

Instruments such as the cartridge injector and microforceps are expensive and are not easily manufactured to be disposable which means that each must be cleaned and sterilized between uses. Because of their sizes and precise construction they are not easily disassembled to facilitate sterilization.

Both instruments are commonly used with a surgical procedure known as phacoemulsification in which an incision is made in the eye to remove a damaged or diseased lens by cutting the lens into pieces and then emulsifying and aspirating the lens particles. Thereafter, a foldable plastic IOL is folded, placed into a cartridge, inserted into a cartridge injector which is then operated to force the lens from the cartridge through the incision into the eye as a replacement for the damaged lens than has already been removed.

The microforceps is used to break the damaged or diseased lens into pieces prior to phacoemulsification. As can be appreciated, these instruments are extremely small in size, particularly given the fact that the incision made in the eye is preferably as small as possible to prevent leakage of eye fluid from the wound after surgery. Where such incisions are sufficiently small, they need not be sutured and will heal without appreciable leakage.

The problem of satisfactorily sterilizing and cleaning microsurgical instruments used in phacoemulsification has been addressed in an article entitled "Residual Debris as a Potential Cause of Post-Phacoemulsification Endophthalmitis," appearing in *Eye* (Basingstroke), Volume 17, No. 4, published May 2003 and written by T. Leslie, D. A. Aitken, T. Barrie, and C. M. Kirkness. The authors conducted a study of phacoemulsification instruments that had been sterilized to determine whether debris had been left behind after typical sterilization operations. Samples were taken from phacoemulsification instruments and from irrigation and aspiration instruments. Two studies were done, each at a different institution.

In the first study, 62 percent of the instruments were found to be clean, 16 percent were found to be moderately contaminated and 22 percent were severely contaminated. The second study produced similar results.

A third study compared instruments that had been cleaned by an automated flushing system prior to sterilization. Although not completely eliminating contamination, the technique of flushing prior to sterilization decreased the incidence of contaminated instruments. The flushing apparatus used was automatic in operation.

The prior art includes examples of attempts to provide means for flushing surgical apparatus prior to sterilization.

U.S. Pat. No. 5,225,001 (Manni) teaches and describes a single channel scope cleaning method and apparatus used to pump sterilizing solution through instruments used for endoscopy and arthroscopy. The cleaning apparatus is placed concentrically about the exterior surface of the probe and sterilizing solution is pumped through the cleaning apparatus and through the channel formed between the cleaner and the endoscopic apparatus.

U.S. Pat. No. 5,279,317 (Bowman) teaches and describes an endoscopic cannulated instrument flushing apparatus for forcing a flushing liquid through an endoscopic cannulated instrument for removal of gross debris. The instrument described in Bowman et al has a handle at one end and a surgical tool, such as a pair of gripping arms, at the other. The handle end remains outside the body while the tool end is inserted through an incision and comes into contact with tissue.

The apparatus has a flushing chamber into which the tool end of the instrument is inserted in a friction fit. Sterilizing flushing fluid is forced into the chamber and through the tool end of the endoscopic instrument to exit out of the handle end. The flow of the flushing liquid is thus from the tool end to the handle end, pushing any debris along the entire length of the instrument, requiring a passage large enough to allow such debris to travel all the way to the handle.

U.S. Pat. No. 5,511,568 (Bowman et al) teaches and describes an endoscopic cannulated instrument flushing apparatus for forcing a flushing liquid through an endoscopic cannulated instrument for removal of gross debris. This patent is a continuation-in-part of the earlier mentioned Bowman et al patent and adds a pressurized source of flushing liquid rather than a hand-operated syringe. As with its parent, the cleaning is done in a direction away from the tool end of the instrument.

None of these references are concerned with microsurgical instruments.

Cartridge injectors have narrow and elongated housings through which a plunger is reciprocated to enter an IOL-holding cartridge and force the IOL out of the cartridge and through an incision into the eye.

Microforceps of the type described herein have pair of surgical steel strips which are placed in face-to-face relationship and along a portion of which a tubular housing is moved or reciprocated during surgery. It is this movement along the protruding surgical strips that may trap debris.

In both cases, the clearance between the outer tubular housing and the plunger or surgical strips is small and any debris trapped therewithin is not only a source for potential infection during a subsequent surgical procedure, but also a source of friction during surgery between moving parts of the respective instruments. This friction changes the "feel" of the instrument to the surgeon because of the extremely small operating field can have a serious effect on the surgery.

The microforceps and cartridge injectors described above are representative of microsurgical instruments which may differ in construction from those described herein but which exhibit the same problems when it comes to cleaning the instruments to remove surgical debris prior to sterilization.

SUMMARY OF THE INVENTION

It is an object of the present apparatus to provide a simply and economically constructed flushing apparatus allowing for the hand-flushing of microsurgical instruments.

It is another object of the present apparatus to provide such apparatus in which the flow of the flushing liquid is toward the operative or distal portion of the instrument rather than toward the proximal or handle portion.

It is yet another object of the present apparatus to provide such apparatus which will flush the microsurgical instrument without requiring the instrument to be significantly disassembled whether or not the instrument has flushing portals.

Yet another object of the present apparatus is to provide a flushing mechanism which will protect the distal ends of the instrument so that they will not be damaged during flushing.

Yet another object of the present apparatus to construct such cleaning apparatus in such a manner in which the actual exit of the flushing liquid can be observed.

While the following describes a preferred embodiment or embodiments of the present apparatus, it is to be understood that this description is made by way of example only and is not intended to limit the scope of the present apparatus. It is expected that alterations and further modifications, as well as other and further applications of the principles of the present apparatus will occur to others skilled in the art to which the apparatus relates and, while differing from the foregoing, remain within the spirit and scope of the apparatus as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further objects and advantages of the present apparatus will be best understood by reference to the accompanying drawings which illustrate use of the apparatus in the best mode presently known.

BRIEF DESCRIPTION OF THE DRAWINGS

The accompanying drawing figures illustrate the apparatus described herein in varying detail and describe details of various embodiments thereof. Drawing figures are exemplary only and are not drawn to scale.

FIG. 1 is a perspective view of a prior art cartridge injector;

FIG. 2 is an exploded view of a similar prior art injector;

DETAILED DESCRIPTION OF THE DRAWINGS

Figure 3:
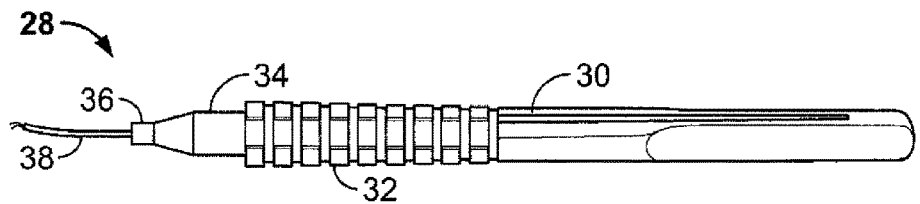
FIG. 3 is a perspective view of a microforceps.

Referring now to FIG. 1, numeral 10 identifies a cartridge injector having an injector body 12, a plunger 14, a finger grip 16, a handle ring 18, a cartridge grip portion 20 and a plunger tip 22. The instrument shown in FIG. 1 is intended to typify cartridge injectors which may vary in construction from injector to injector but which generally include, the foregoing or similar components.

Referring now to FIG. 2, an exploded view of an injector similar to that of FIG. 1 better illustrates the individual components of such an injector including cylindrical end housing 24. As shown in FIG. 2, plunger tip 22 and plunger 14 are attached one to the other such that when plunger 14 is advanced so is plunger tip 22. As also shown in FIG. 2, handle ring 18 is held in a friction fit to knob 26 and can easily be removed.

Referring now to FIG. 3, the numeral 28 identifies a microsurgical forceps having right and left handles 30, 32, nose 34, tube grip 36 and tube 38.

Figure 4:
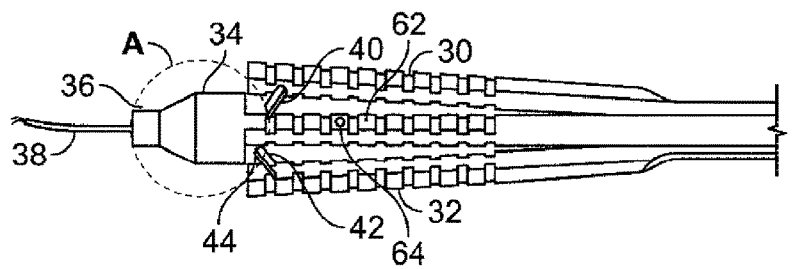
FIG. 4 is a partial view of the instrument of FIG. 3 showing the handles extended.

Referring now to FIG. 4, handles 30, 32 are shown in greater detail. Handles 30, 32 are shown in their "open" position and can be moved to a "closed" position by squeezing handles 30 and 32 simultaneously.

Also shown in FIG. 4 are right and left links 40, 42 attached, respectively, to handles 30, 32. Links 40, 42 are also attached to slider block 44, partially shown in FIG. 4. Typically, when handles 30, 32 are squeezed, linkages 40, 42 and slider block 44 forward move tube grip 36 forward, thereby moving tube 38 forward.

Figure 5:
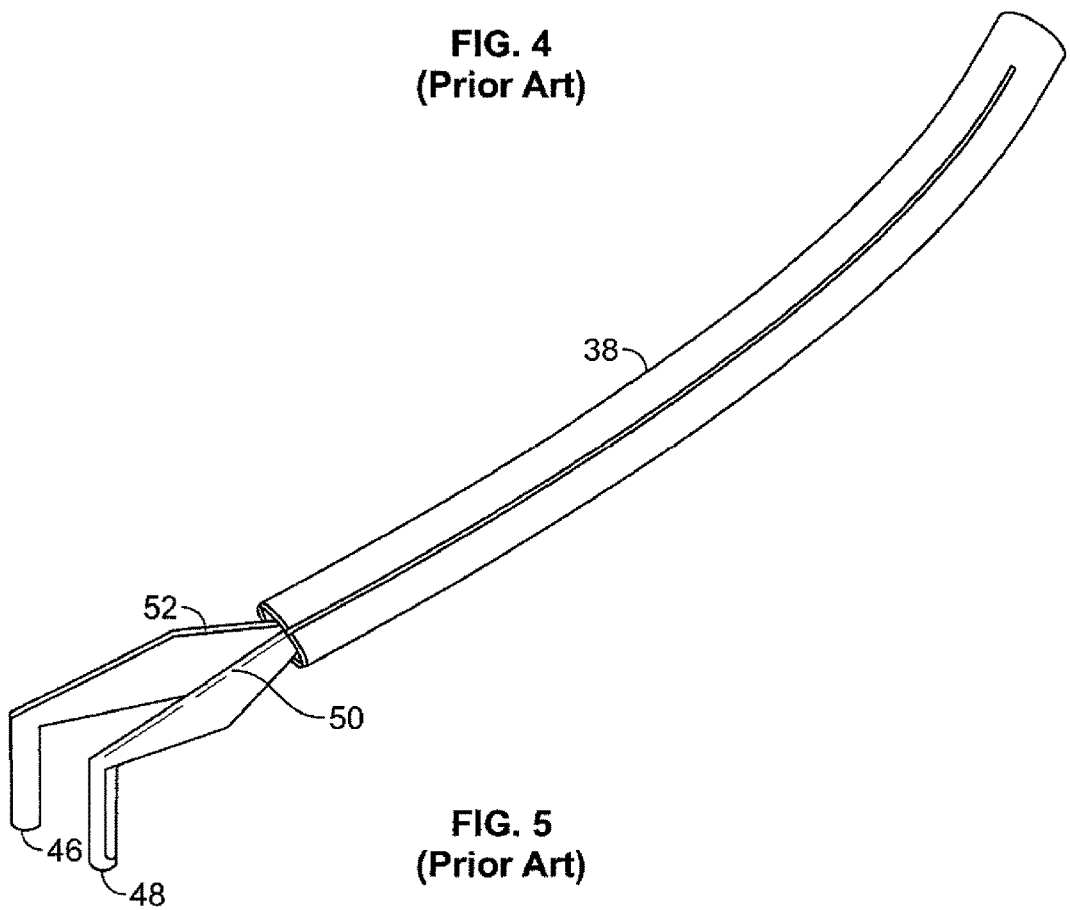
FIG. 5 is an enlarged view of the tube of the instrument in FIG. 3.

Referring to FIG. 5, tube 38 is shown in greater detail as are right and left forceps tips 46, 48. Tip 46 is formed on a spring steel strip 52 and is the terminus of strip 52, while forceps tip 48 is formed on spring steel strip 50 and is the terminus of strip 50.

As constructed, strips 50, 52 are biased to separate one from the other when unconstricted. As handles 30, 32 are squeezed and tube 38 is moved forward, strips 50, 52 are pushed one towards another until, when they meet, tip 46 and 48 form a single unitary tip. Conversely, as handles 30, 32 are released, tube 38 is drawn rearward and tips 46, 48 return to their separated position, thus providing an alternating gripping and release action.

Figure 6:
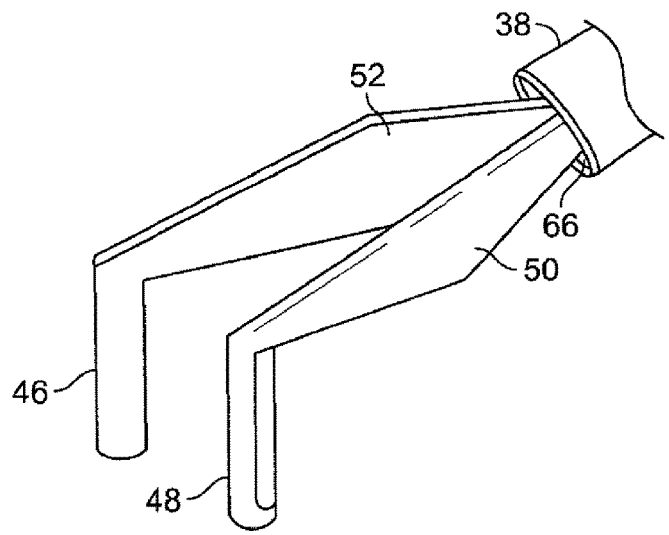
FIG. 6 is an enlarged view of the end portion of the tube of FIG. 5.

Referring now to FIG. 6, an enlarged view of tips 46, 48 are shown as well as an enlarged portion of strips 50, 52, and illustrating the relationship between strips 50, 52 and tube 38. As seen, strips 50, 52, do not occupy the entire inner space of tube 38, leaving an annular void volume within which debris can be trapped as tube 38 is progressively advanced and retracted.

Figure 7:
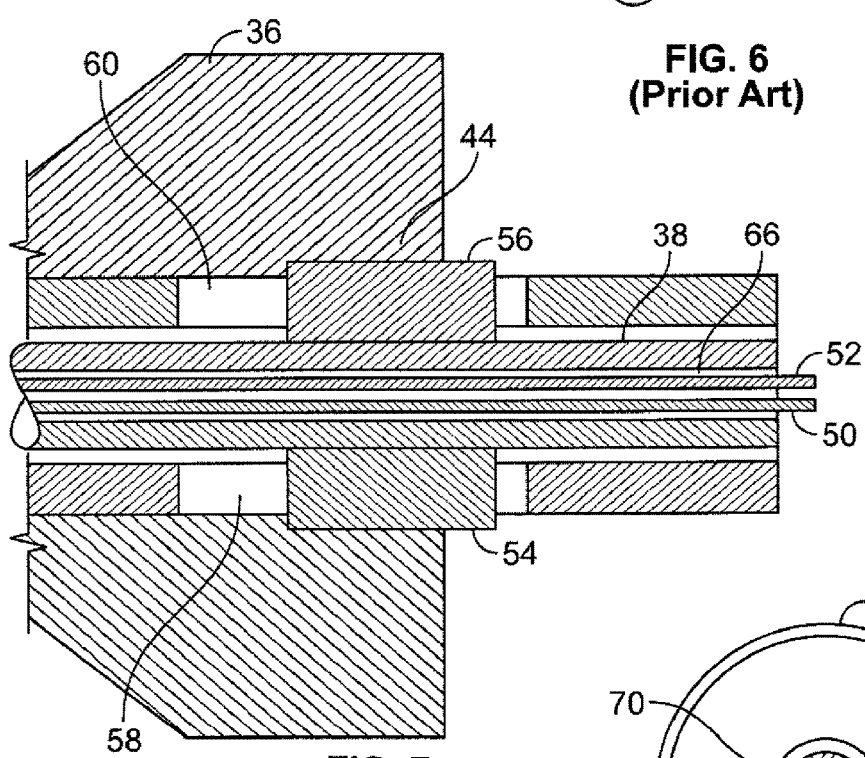
FIG. 7 is a sectional view of detail A of FIG. 4.

Referring now to FIG. 7, a sectional view is shown of slider block 44 showing right and left link blocks 54, 56 which grip tube 38 and, in this embodiment, are also attached to tube grip 36. Tube 38 is movable along the distance provided by right and left slots 58, 60. As shown here schematically, right and left strips 50, 52 extend past slider block 44 and are secured within housing 62 by screws 64 as shown in FIG. 4.

As illustrated in FIG. 7, there is a void volume indicated by the numeral 66 comprising a general annular space around strips 50, 52.

Figure 8:
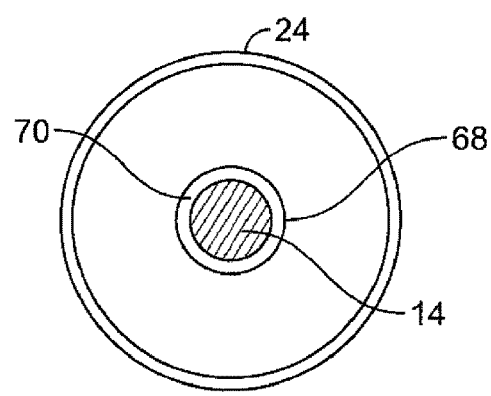
FIG. 8 is a view along 8-8 of FIG. 2.

Referring to FIG. 8, a view taken at 8-8 of FIG. 2 is shown of cartridge injector and housing 24 showing a plunger aperture 68 formed therethrough through which plunger 14 passes.

A space 70 is created by the difference between the outer diameter of the plunger 14 and the inner diameter of the plunger aperture 68.

Figure 9:
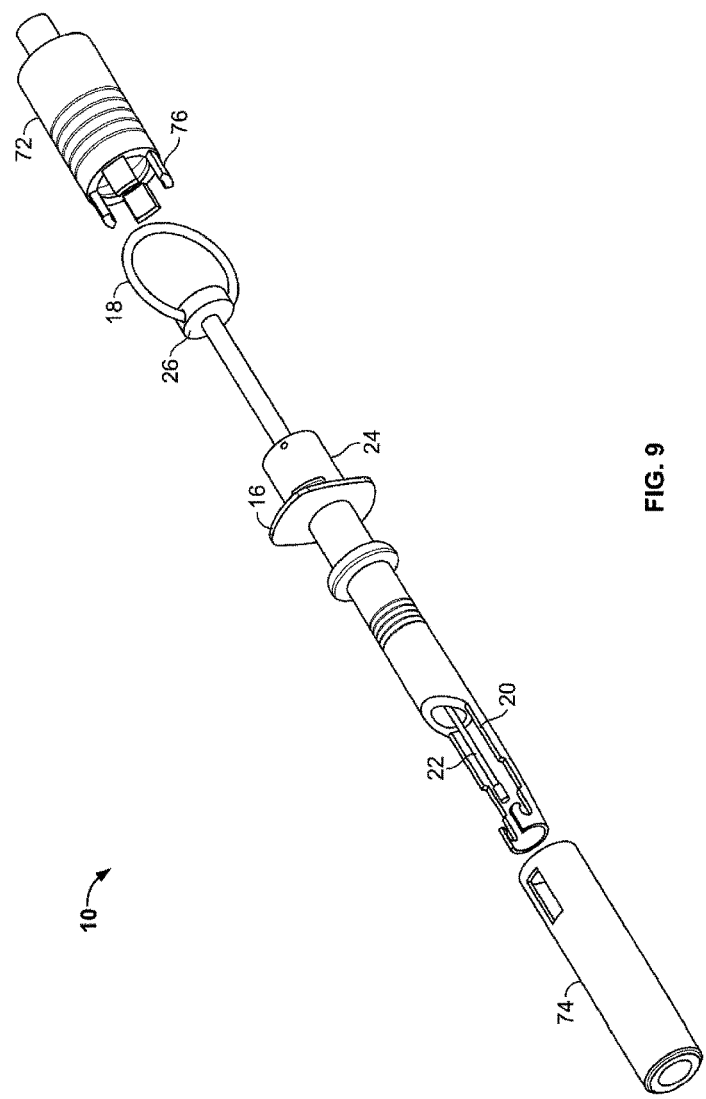
FIG. 9 is a view of a first embodiment of the present invention.

Referring now to FIG. 9, a first embodiment is shown as a microsurgical instrument cleaning apparatus intended for use with injector 10. As shown, the cleaning apparatus comprises an inlet plug 72 and a tip protector 74, sized and dimensioned to fit injector 10 as described below.

In FIG. 9, inlet plug 72 and tip protector 74 are shown in spaced relationship to injector 10 prior to being attached to injector 10. Protector 74 slips onto the cartridge grip portion 20 of injector 10 in a friction fit and is intended to protect plunger tip 22 during cleaning. Prior to applying inlet plug 72 to injector 10 handle ring 18 is removed from knob 26 and will be reinstalled after flushing.

Figure 10:
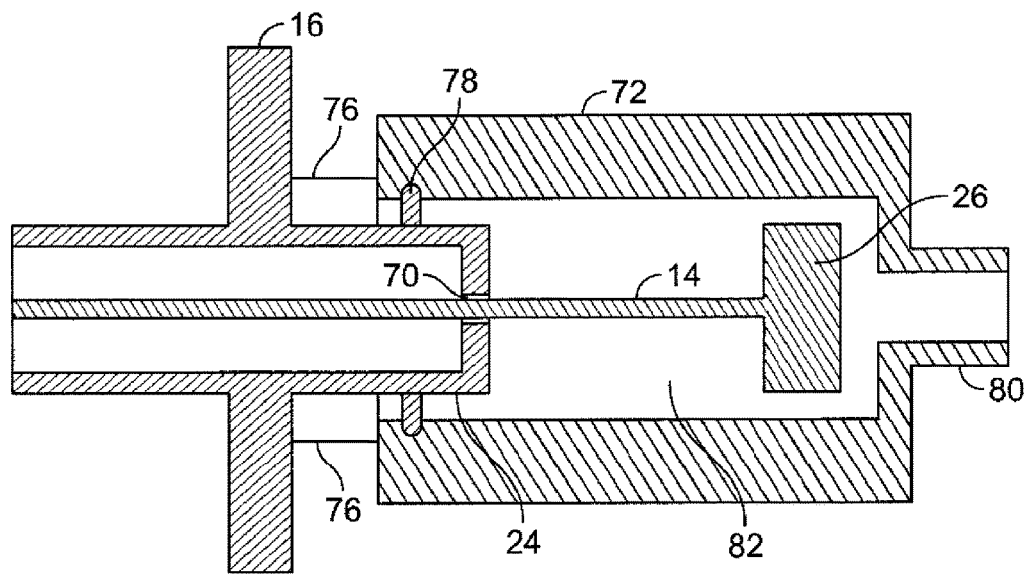
FIG. 10 is a sectional view showing attachment of the inlet plug to the instrument of FIG. 9.

Referring now to FIG. 10, inlet plug 72 is shown as attached to injector 10. As seen in FIG. 10, inlet plug 72 is pushed onto end housing 24 in a friction fit and is engaged in a liquid tight seal by O-ring 78. A series of plug legs 76 shown in FIGS. 9 and 10 help to position inlet plug 72 by abutting and contacting finger grip 16. When applied, it can be seen that plunger 14 and knob 26 are disposed within inlet plug 72.

Because plunger 14 may have to be partially pushed in to fit within inlet plug 72, it is likely that plunger tip 22 will likewise be extended past cartridge holding portion 20 yet will remain within tip protector 74.

As seen in FIG. 10, inlet plug 72 has an inlet port 80 formed integrally therewith. In order to effectuate flushing of injector 10. After inlet plug 72 has been press-fit to end housing 24, a hand held syringe (not shown) is inserted into port 80 and a flushing liquid is forced from the syringe through port 80 and through the interior cavity 82 of inlet plug 72. The liquid is prevented from exiting inlet plug 72 by O-ring 78 and instead, is forced through space 70 along the entire length of injector 10, exiting about tip 22. In this manner, the flushing liquid contacts any debris held within injector 10 proximate cartridge holding portion 22 and forces it out in a direction opposite to that in which the debris was drawn into injector 10. This avoids the necessity of having to force both the flushing liquid and any debris from cartridge holding portion 20 through the entire body of injector 10 to exit at tolerance base 70. Thus, debris is flushed out from injector 10 covering the shortest possible distance and through spaces that are larger than space 70.

Figure 11:
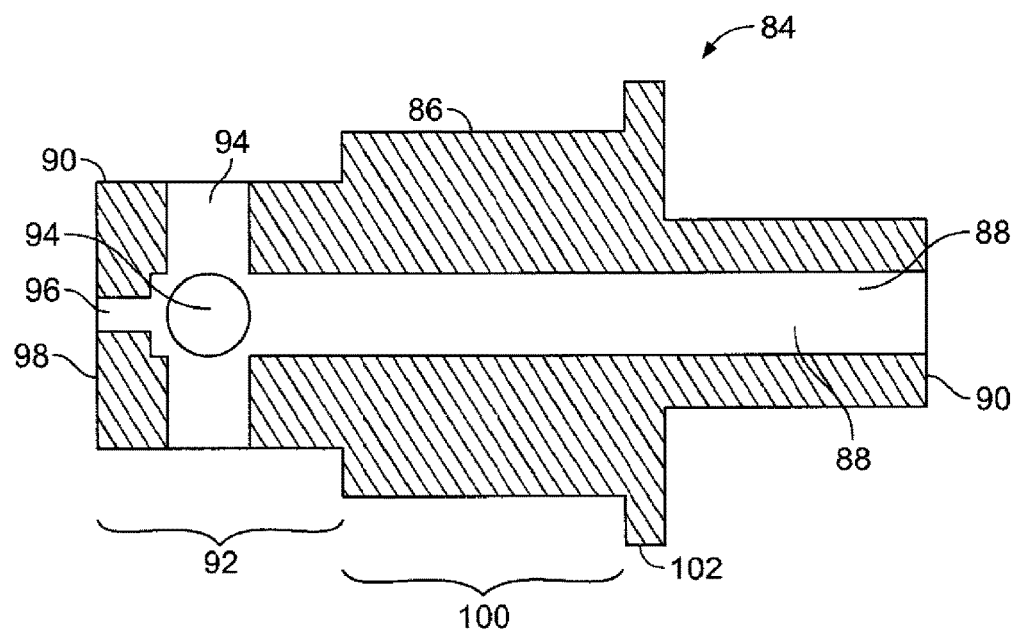
FIG. 11 is a sectional view of the inlet plug used in a second embodiment of the present apparatus.

Referring now to FIG. 11, a second embodiment of the present apparatus is shown, particularly adapted for use in flushing a microsurgical forceps such as that shown at numeral 28 of FIG. 3. In FIG. 11, a flush plug 84 is shown having a generally solid thermoplastic body 86 through which a flush channel 88 is formed. Flush channel 88 extends from an inlet port 90 to a flushing portion 92 through which a pair of flush ports 94 are formed. In this embodiment, flush ports 94 are circular in cross section and are formed at right angles one to the other exiting the lateral sides of flush portion 92. A fluid outlet 96 is formed at the terminus 98 of flushing plug 84. Integrally formed with flushing portion 92 is tube grip portion 100 which, in turn, is integrally formed with tube stop 102 which, in turn, is integrally formed with inlet port 90.

Figure 12:
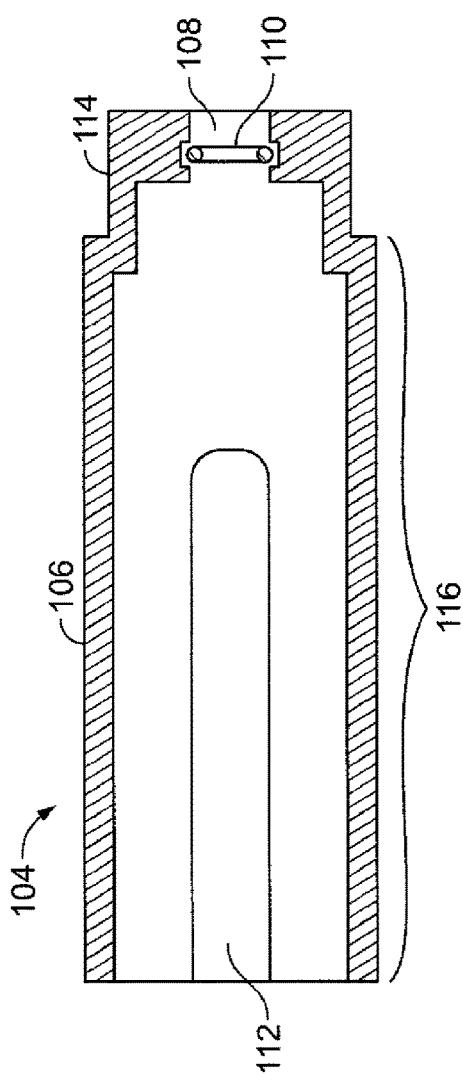
FIG. 12 is a perspective view of the outlet plug used in the second embodiment of the present apparatus.

Referring now to FIG. 12, a tip protector 104 is shown, having a one-piece, hollow, cylindrical body 106 with a tip inlet 108 formed at one end thereof. An O-ring 110 is disposed within tip inlet 108. As also seen in FIG. 12, an observation slot 112 is formed in body 106. Preferably, a pair of observation slots 112 are formed opposite one another, as more clearly shown in FIG. 16. As seen in FIG. 12, the protector 104 has a tube grip portion 114 formed integrally with protector portion 116.

Figure 13:
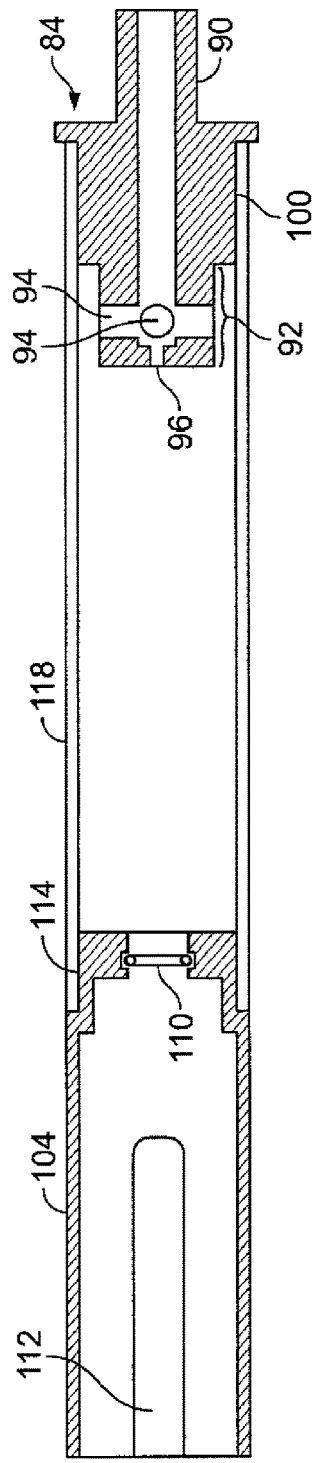
FIG. 13 is a lateral sectional view of the second embodiment of the present apparatus showing the inlet and outlet plugs attached to the flush chamber.

Referring now to FIG. 13, flush plug 84 and tip protector 104 are shown assembled to a transparent, cylindrical flush tube 118. As seen in FIG. 13, flush tube 118 is fluid tightly attached to flush plug 84 at tube grip portion 100 while protector 104 is fluid tightly attached to flush tube 118 at tube grip portion 114. Fluid tight attachment can be achieved in a friction fit between flushing plug 84, protector 104, and flush tube 118. A fluid tight fit can also be achieved by forming screw threads along the interior portion along the ends of flush tube 118 with mating screw threads formed on the exterior surfaces of tube grip portions 100, 114, respectively.

As seen in FIG. 13, flushing portion 92 of flush plug 84 is smaller in diameter than tube grip portion 100 leaving a space between the inner walls of flush tube 118 and flush ports 94.

Use of the second embodiment of the present apparatus as a cleaning tool for a microsurgical forceps may now be described.

Protector 104 is removed from flush tube 118 and is attached to forceps 28. Nose 34 is inserted through tip inlet 108 until it passes through and is gripped by O-ring 110 in a liquid tight fit. Handles 30, 32 are held in the open position as shown in FIG. 4, thereby exposing links 40, 42 and slider block 44.

Figure 14:
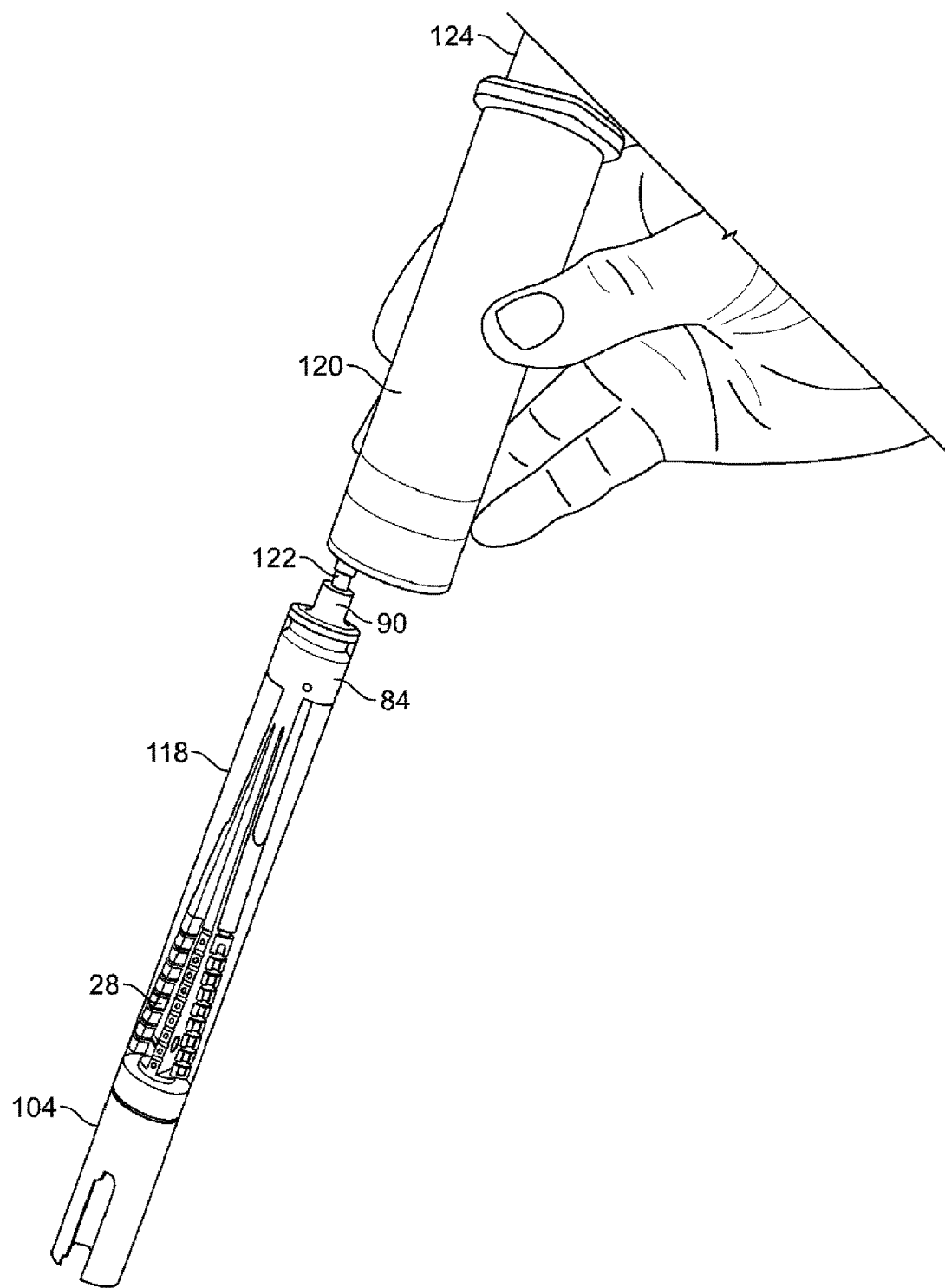
FIG. 14 is a perspective view showing the instrument of FIG. 3 inserted in the flush chamber for cleaning.
Figure 16:
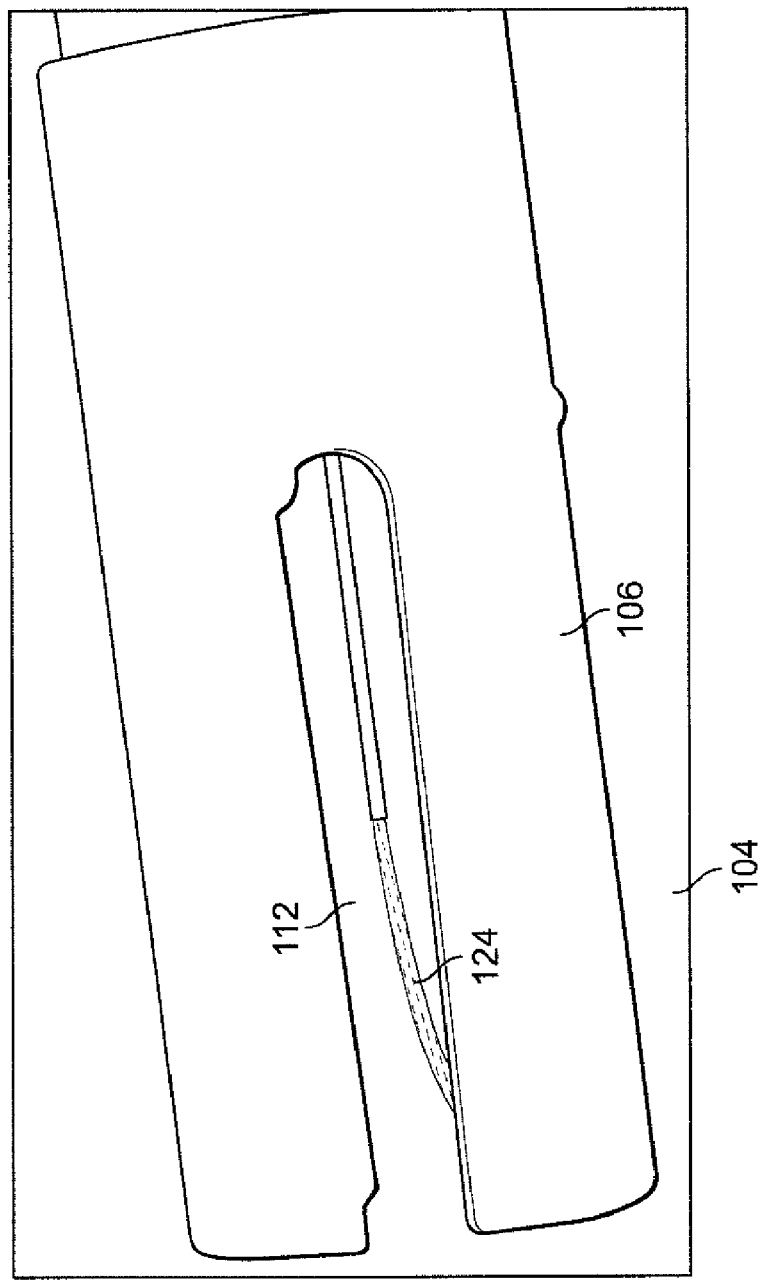
FIG. 16 is an enlarged detail of the outlet plug of FIG. 15 showing the flow of flushing liquid.

Holding protector 104, forceps 28 is then placed within flush tube 118 as shown in FIG. 14 until protector 104 engages flush tube 118 in a liquid tight fit. A syringe 120 filled with flushing liquid is attached via syringe tip 122 to inlet port 90. As plunger 124 on syringe 120 is pushed flushing liquid enters inlet port 90 and proceeds to fill the interior of flush tube 118 allowing the flushing liquid to reach slider block 44 and, thereby, void volume 66 surrounding strips 50, 52 within tube 38. The flushing liquid is then forced along tube 38 until it exits in a flush stream 124 as shown in FIG. 16. Flush stream 124 is visible through observation slots 112 and thereby assures the user that flushing liquid is, indeed, being forced through forceps 28.

In this manner, any debris trapped within tube 38 or on tips 50, 52 is flushed away from the interior of forceps 28 rather than toward the interior thereof. Use of flush tube 118 creates a fluid flow path from syringe 120 through annular void volume 66 creating the flushing effect. It would otherwise be virtually impossible to insert any type of syringe or other flushing apparatus to effectively flush tube 28 from the interior side thereof as opposed to the exterior side.

Figure 15:
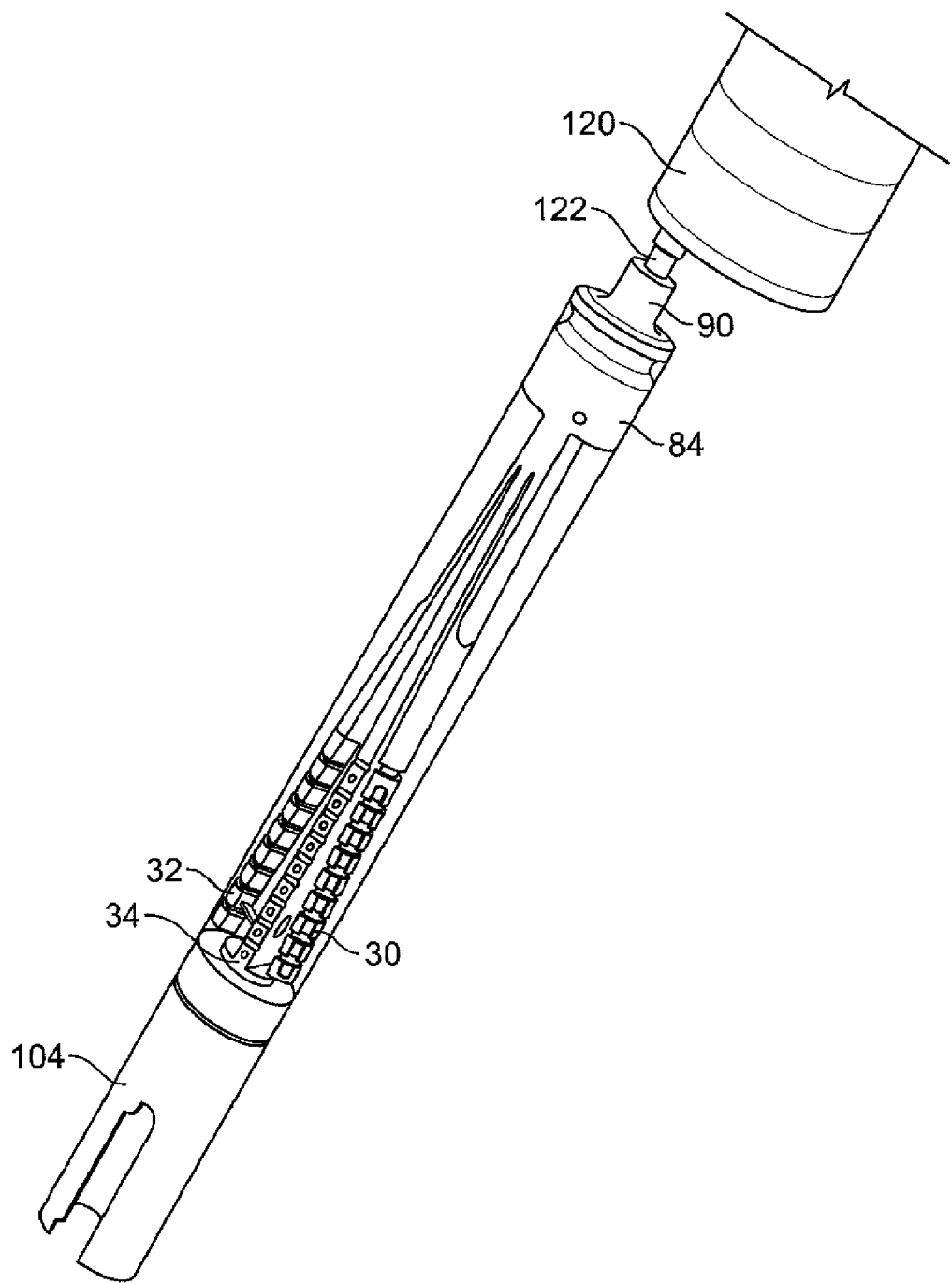
FIG. 15 is an enlarged detail of FIG. 14.

In FIG. 15, an enlarged view of the assembled apparatus in FIG. 14 is shown more clearly illustrating the open position of handles 30, 32 and the engagement of nose 34 with protector 104.

Figure 17:
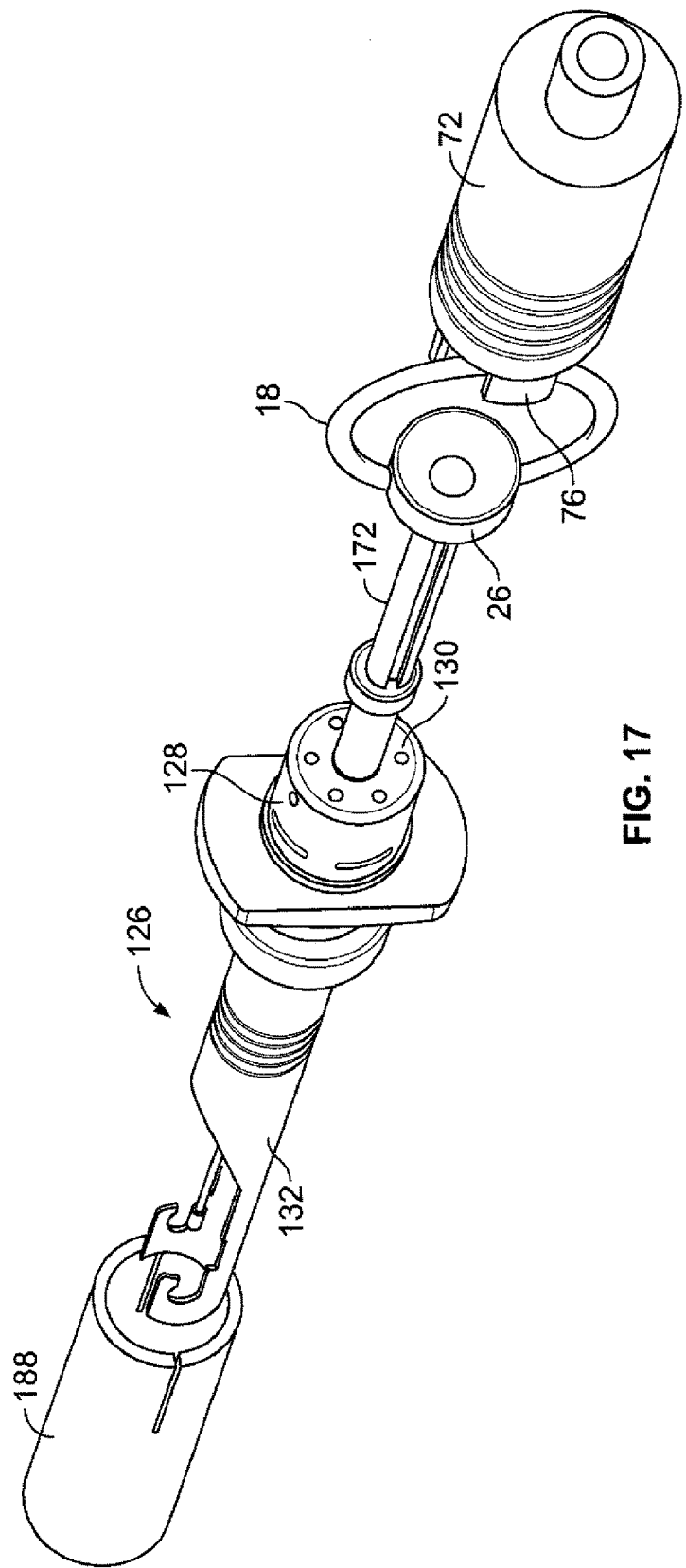
FIG. 17 is a perspective view of an injector with a modified end cap.
Figure 18:
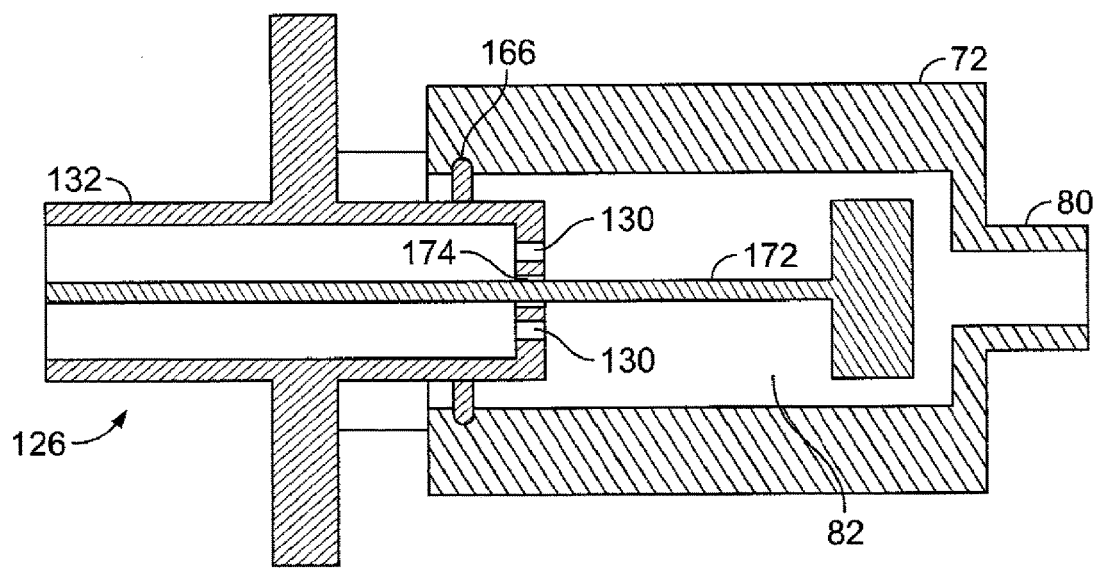
FIG. 18 is a lateral sectional view of the end cap attached to the injector of FIG. 17.

Referring now to FIG. 17 the numeral 126 identifies an injector with an end housing 128 having a series of flush channels 130 formed therethrough. As seen in FIG. 18, channels 130 provide flow passages for flushing liquid forced through inlet 80 into interior cavity 82 and through barrel 132 of injector 126. While FIG. 17 shows channels 130 arranged in a circular pattern with six channels other numbers and patterns of channels can be used as desired.

As described hereinabove, inlet plug 72 is secured to end housing 128 in a friction fit after ring 18 is removed from knob 26, and is held in a liquid-tight fit by O-ring 166. Flushing then proceeds as described above.

Figure 19:
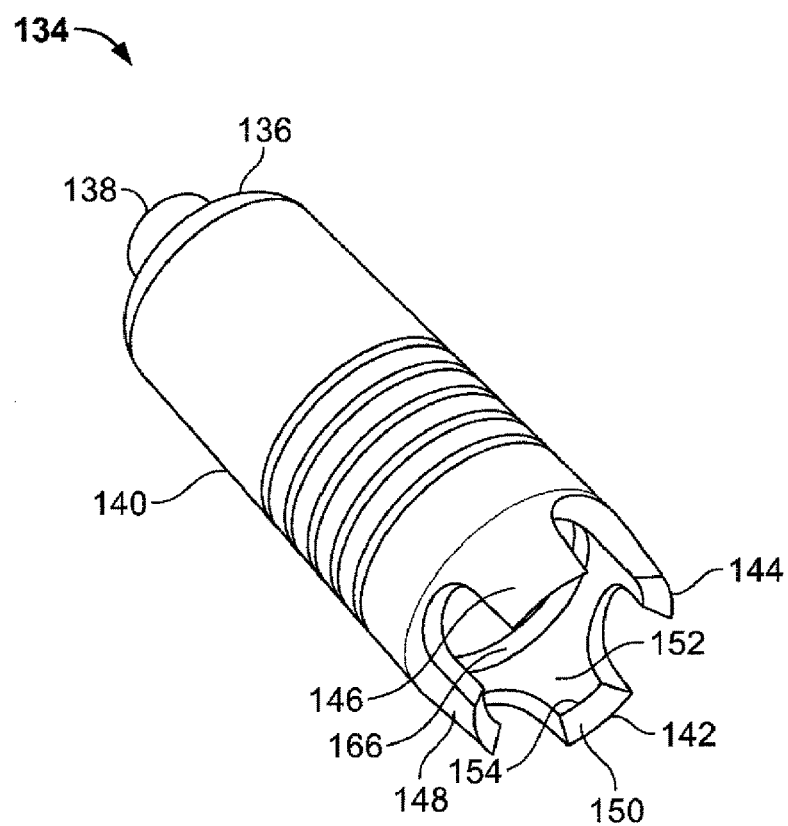
FIG. 19 is a perspective view of another embodiment of an inlet plug.

Referring now to FIG. 19 the numeral 134 identifies another embodiment of an inlet plug having an inlet end 136 with an inlet port 138 and a hollow body 140, terminating in a series of mounting fingers 142, 144, 146 and 148. Finger 142 is exemplary of the others and will be described in detail.

Finger 142 is formed integrally with plug 134 and has a latch end 150 formed along an interior surface 152. A latch ridge 154 is formed on and tapers upward from surface 152. When a sufficient force is exerted on latch end 150 finger 142 will flex slightly.

Figure 20:
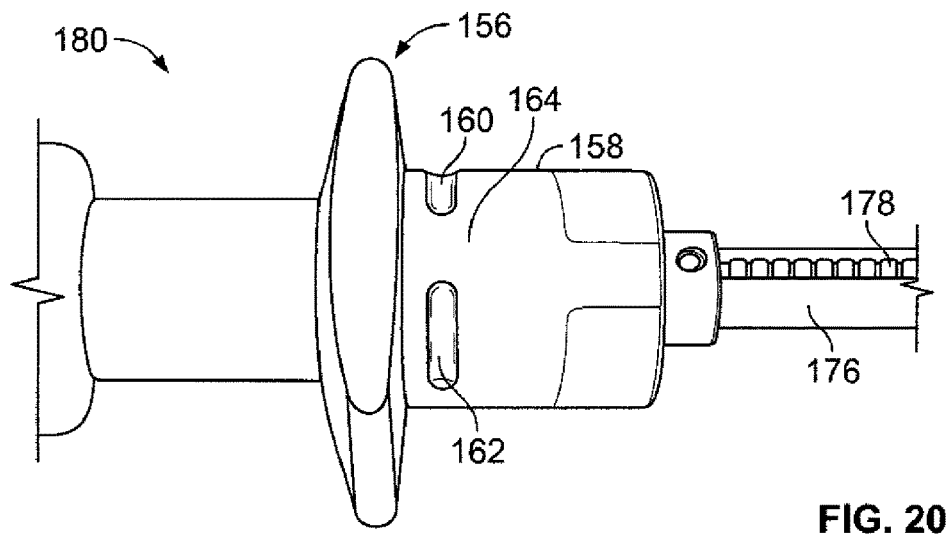
FIG. 20 is a lateral view of an instrument having mounting grooves formed thereon.

Referring now to FIG. 20, the numeral 156 identifies a portion of the plunger end of a microsurgical instrument constructed in accordance with the foregoing descriptions. End housing 158 of plunger end 156 has formed on its surface a series of mounting depressions or grooves such as shown at 160, 162, formed as shallow depressions in end housing 158. Groove 160 is positioned to register with latch ridge 154 of finger 142 and it should be understood that the number and position of each such groove is selected to register with one such finger 142, 144, 146 or 148. While four such grooves are shown, it should be appreciated that other numbers and configurations of fingers can be selected. Similarly, the number and position of grooves formed on end housing 158 preferably register with said fingers when inlet plug 136 is mounted to end housing 158.

Preferably, fingers 142, 144, 146 and 148 of plug 136 engage end housing 158 at those portions 164 intermediate grooves 160, 162. Thereafter, inlet plug 134 is rotated to move each finger to register with one groove, snapping latch ridges such as 154 into each such groove to hold inlet plug 134 firmly to end housing 158. As seen in FIGS. 18 and 19, an O-ring 166 is positioned within inlet plug 134 to provide a liquid-tight contact with the outer surface of end housing 158 as described above.

Figure 21:
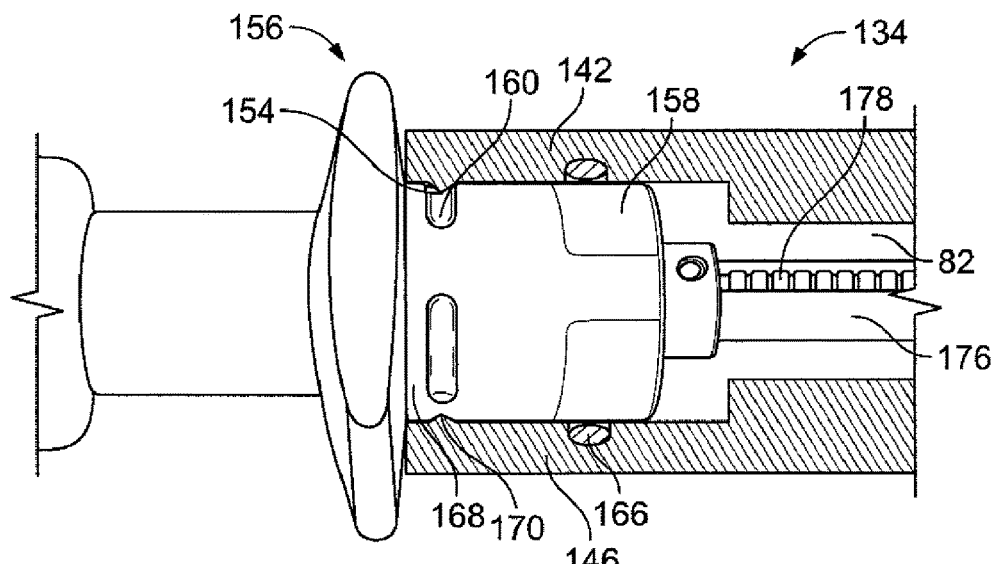
FIG. 21 is a view of the inlet plug of FIG. 19 shown in section and attached to the instrument of FIG. 20.

Referring now to FIG. 21, inlet plug 134 is shown in section, with fingers 142, 146 engaging, respectively, grooves 160, 168, with latch ridges 154, 170 engaging, respectively, grooves 160, 168. O-ring 166 is also shown gripping the outer surface of end housing 158 to form a liquid-tight seal.

One considerable advantage of forming flush channels 130 such as those shown at FIGS. 17 and 18 is to allow flushing liquid to enter a microsurgical instrument independent of how the plunger is articulated with respect to the instrument housing. As an example, in FIG. 18 plunger 172 is shown in a friction fit with both the bore 174 of the instrument and plunger 172 being smooth. In such a configuration, if enough flush liquid can be forced between the plunger and the bore flush channels may or may not be required. However, if an increased volume of flush liquid is desired then flush channels 130 will provide additional flow capacity.

In FIGS. 20 and 21, plunger 176 has an internally-mounted spring 178 which is compressed when plunger 176 is pushed into instrument 180 and which, when released, moves plunger 176 out from instrument 180. When either inlet plug 72 or 134 is used with such a plunger, spring 178 is disposed within interior cavity 82 and will be contacted by and cleaned with the flush liquid entering via inlet port 80 or 138.

Figure 22:
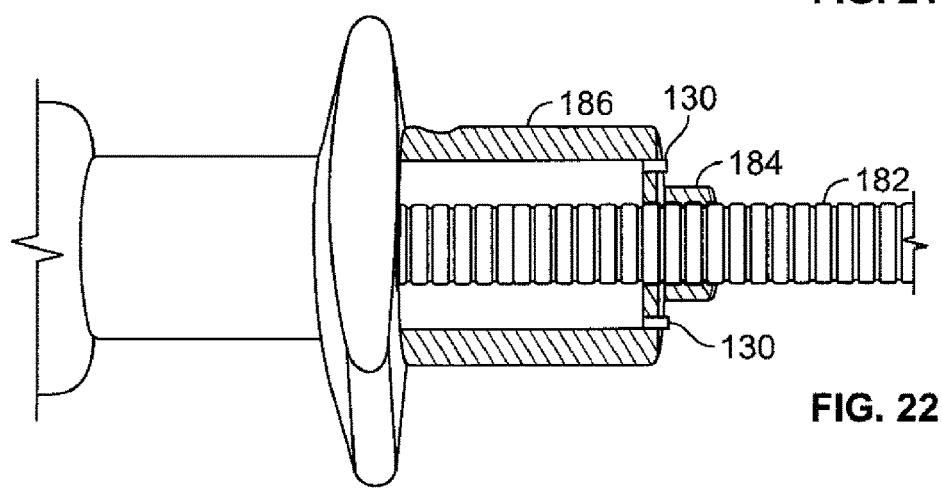
FIG. 22 is a partial sectional view of a microsurgical instrument having a threaded plunger.

Referring now to FIG. 22, plunger 182 has screw threads formed along its length and is rotated through a threaded opening 184 in end housing 186. For such a construction the increased difficulty of forcing flushing liquid past such screw threads makes the presence of flush channels 130 extremely advantageous to allow the flushing liquid to enter the instrument. Thus, no matter how the plunger is fitted to the instrument, the presence of flush channels 130 allows flushing liquid to enter and clean the instrument as described above.

Referring again to FIG. 17 the numeral 188 identifies an end plug shaped and configured to engage barrel 132 in a friction fit. End plug 188 acts as a protective sheath for the instrument when it is being flushed and to protect the user from coming into contact with any sharp cutting surface carried by the instrument.

While the foregoing has described a hand-held syringe as a preferred source for the flushing liquid, other sources can be used as well. One example is a fluid reservoir having an outlet tube or conduit adapted to be attached to the inlet ports described above. A manual or powered pump or other liquid motive device may then be used to force the liquid from the reservoir to the inlet port. The reservoir may also be elevated and gravity may be used as a feed to move the liquid.

What is claimed is:

1. An apparatus for cleaning a surgical instrument, said instrument having a body with a proximal end and a distal end, an internal passageway having an outlet at said instrument body distal end, and a tip at said body distal end for contacting a patient, said apparatus comprising:

a hollow chamber extending between proximal and distal ends, said chamber proximal end having a flushing liquid inlet port; and a tip protector attachable to said chamber distal end, said tip protector having at least a first seal adapted to provide a liquid-tight fit around said instrument distal end with said instrument substantially within said chamber, wherein with the tip protector assembled with the hollow chamber said tip of said instrument extends through a portion of said tip protector;

whereby a flushing liquid injected into said inlet port enters said chamber adjacent said instrument proximal end, said flushing liquid passes through said chamber and said instrument internal passageway, and said flushing liquid exits said instrument body distal end through said outlet of said instrument internal passageway whereby a contaminant in said instrument is flushed in a direction away from said instrument proximal end and out of said instrument internal passageway outlet, wherein said tip protector has at least one observation window therein, wherein said flushing liquid exiting said instrument tip is visible through said observation window.

2. The apparatus of claim 1, wherein said chamber extends axially between said chamber proximate and distal ends, and said flushing liquid inlet port directs said flush liquid axially into said chamber.

3. The apparatus of claim 1, wherein said at least one observation window has the form of a slot.

4. The apparatus of claim 1, wherein said tip protector is threadably attached to said chamber distal end.

5. The apparatus of claim 1, further comprising a sealing means at said chamber proximal end, said sealing means for creating a liquid tight seal at said flushing liquid inlet port.

6. The apparatus of claim 5, wherein said sealing means is a plug.

7. The apparatus of claim 6, wherein said plug has at least one aperture permitting said flushing liquid to enter said chamber.

8. The apparatus of claim 7, further comprising at least one flush port extending radially within said plug and in communication with said at least one aperture, whereby said at least one flush port permits said flushing liquid to enter said chamber in a radial direction.

9. The apparatus of claim 5, wherein said sealing means is a threaded connection between said chamber proximal end and a flushing liquid source.

10. The apparatus of claim 9, wherein said flushing liquid source is a hand-held syringe.

11. The apparatus of claim 1, wherein said chamber is cylindrical.

12. An apparatus for cleaning a surgical instrument, said instrument having a body with a proximal end and a distal end, an internal passageway having an outlet at said instrument body distal end, and a tip at said body distal end for contacting a patient, said apparatus comprising:

a hollow chamber extending between proximal and distal ends, said chamber proximal end having a flushing liquid inlet port; and a tip protector attachable to said chamber distal end, said tip protector having at least a first seal adapted to provide a liquid-tight fit around said instrument distal end with said instrument substantially within said chamber, wherein with the tip protector assembled with the hollow chamber said tip of said instrument extends through a portion of said tip protector;

whereby a flushing liquid injected into said inlet port enters said chamber adjacent said instrument proximal end, said flushing liquid passes through said chamber and said instrument internal passageway, and said flushing liquid exits said instrument body distal end through said outlet of said instrument internal passageway whereby a contaminant in said instrument is flushed in a direction away from said instrument proximal end and out of said instrument internal passageway outlet, wherein said tip protector further comprises a second seal, said second seal providing a liquid-tight fit between said chamber distal end and said tip protector, and at least one observation window in said tip protector, wherein said flushing liquid exiting said instrument tip is visible through said observation window.

* * * * *